United States Patent [19]

Tölg et al.

[11] 4,081,345
[45] Mar. 28, 1978

[54] APPARATUS FOR DETERMINING SMALL AMOUNTS OF NITROGEN

[75] Inventors: Günter Tölg; Wido Werner, both of Schwabisch Gmund, Germany

[73] Assignee: Max-Planck-Gesellschaft zur Foerderung der Wissenschaften e.V., Gottingen, Germany

[21] Appl. No.: 710,233

[22] Filed: Jul. 30, 1976

[30] Foreign Application Priority Data

Aug. 4, 1975 Germany .................... 2534773

[51] Int. Cl.² ................................ G01N 27/44
[52] U.S. Cl. ...................... 204/195 T; 204/195 R; 204/1 T; 23/230 R; 23/230 M; 23/253 R
[58] Field of Search .............. 204/1 N, 195 R, 195 T; 23/230 R, 232 E, 253 R, 254 E, 255 E, 230 M

[56] References Cited

U.S. PATENT DOCUMENTS

| | | | |
|---|---|---|---|
| 3,131,133 | 4/1964 | Barendrecht | 204/195 T |
| 3,361,661 | 1/1968 | Schulze | 204/195 T |
| 3,461,042 | 8/1969 | Martin et al. | 204/1 N |
| 3,497,322 | 2/1970 | Boys | 204/1 N |
| 3,580,832 | 5/1971 | Rhodes | 204/195 T |
| 3,616,273 | 10/1971 | Oita | 204/1 N |
| 3,716,334 | 2/1973 | Pont | 204/195 T |

*Primary Examiner*—T. Tung
*Attorney, Agent, or Firm*—Hans Berman

[57] ABSTRACT

The nitrogen content of a substance is determined by digesting the substance in a sealed container at superatmospheric pressure in a liquid acid medium until the nitrogen is converted to ammonium ions, the medium is alkalinized, and the ammonia liberated thereby is driven from the alkalinized medium into an acidic aqueous medium by steam distillation in a closed system in which the steam used is generated from the acidic aqueous medium. The latter then is adjusted to a weakly alkaline pH, and the ammonia present is oxidized to nitrogen by hypobromite ions electrolytically generated from bromide ions in the adjusted solution. The amount of current consumed is determined as a measure of the nitrogen originally present.

2 Claims, 4 Drawing Figures

Fig.1
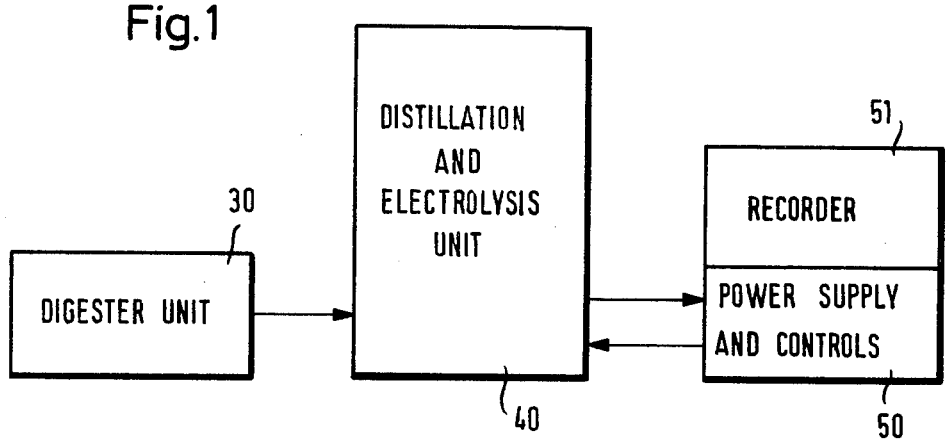
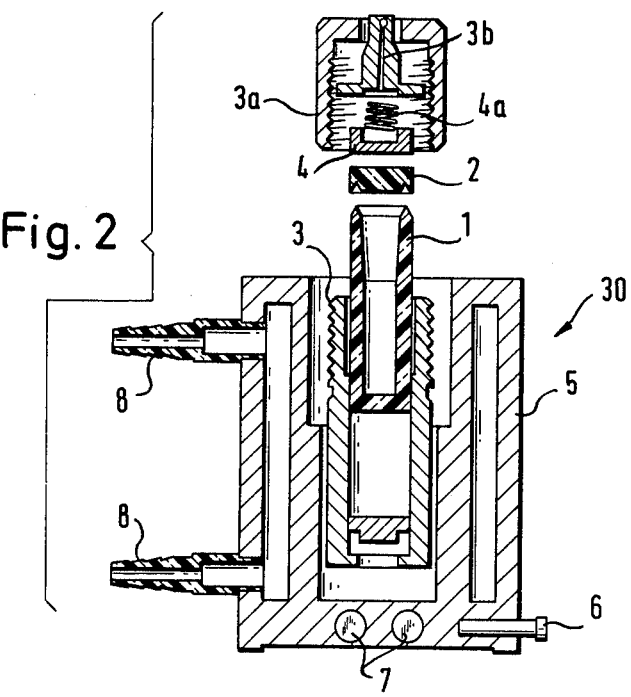
Fig. 2

APPARATUS FOR DETERMINING SMALL AMOUNTS OF NITROGEN

This invention relates to a method of analyzing a substance for minute amounts of nitrogen and to apparatus for performing the method.

It has long been known from the work of Kjeldahl to digest the substance to be analyzed by means of a liquid acid medium, alkalinizing the digestion mixture, distilling the ammonia liberated from the mixture together with water vapor, and determining the amount of the ammonia as a measure of the nitrogen originally present. The original method of Kjeldahl and its modern variations are limited in the amounts of nitrogen capable of direct determination by the impurities unavoidably present in the reagents and other materials employed. When extremely small amounts of nitrogen are to be determined, it is necessary to compensate for the effects of such impurities which must be determined separately. Calibration by means of known specimens is unavoidable in all spectroscopic methods of nitrogen determination.

It is the primary object of this invention to permit the determination of nitrogen by a modified Kjeldahl procedure without significant errors being introduced by the materials employed even if the nitrogen content of the analyzed substance is less than 1 p.p.m., and to avoid the need for determination of error introduced by reagents or other calibration.

At the core of this invention is the use of a minimum amount of reagents and other potential sources of nitrogeneous contaminants. Thus, the substance to be analyzed is digested in a sealed container at superatmospheric pressure which permits the amount of digesting acid to be reduced to a fraction of the conventionally necessary amounts. The steam distillation of the alkalinized digestion mixture is performed in a closed system in which the steam required is generated in the acidic aqueous solution employed for absorbing the ammonia liberated from the digestion mixture. Ammonia is determined in the absorption liquid at slightly alkaline pH by electrolytically converting bromide ions to hypobromite ions which oxidize the ammonia to nitrogen, the amount of current consumed in producing the hypobromite ions being determined as a measure of the nitrogen originally present in the analyzed substance.

In another aspect, the invention also resides in apparatus employed for performing the steam distillation, the absorption, and the converting of bromide to hypobromite. The apparatus includes a distilling vessel adapted to hold the alkalinized digestion mixture, a receiver adapted to hold the acidic aqueous medium, and independently operated heaters for the vessel and receiver. First connecting tubing connects the vessel to the receiver for introducing the material of vapors generated in the heated vessel into the acidic medium in the receiver, and second connecting tubing connects the receiver to the vessel for introducing steam generated in the receiver into the contents of the vessel. A condenser interposed between the first tubing and the receiver condenses the material of the vapors to liquid. Electrodes project into the receiver.

Other features, additional objects, and many of the attendant advantages of this invention will readily be appreciated as the same becomes better understood from the following detailed description of preferred embodiments when considered in connection with the appended drawing in which:

FIG. 1 is a block diagram of apparatus for carrying out the method of the invention;

FIG. 2 shows the digester unit in the apparatus of FIG. 1 in exploded, elevationally sectional view;

Figure 3:
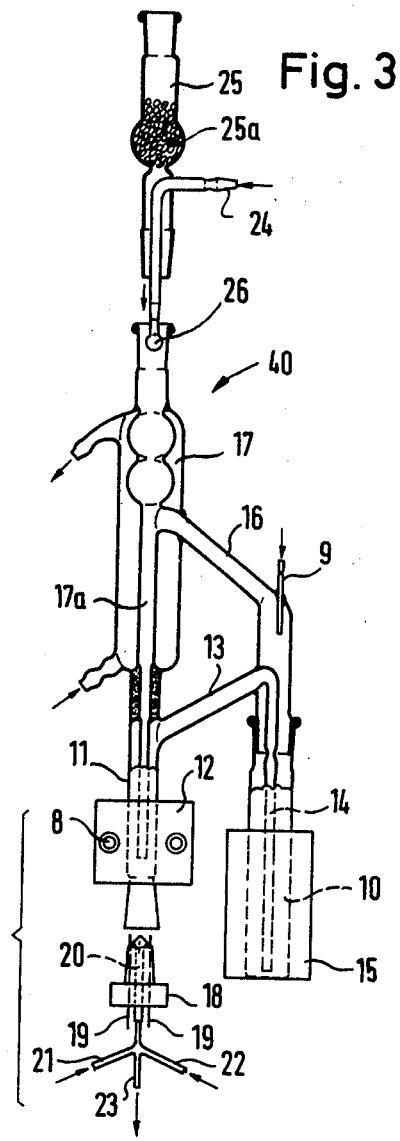
FIG. 3 is a similar view of the distillation and electrolysis unit in the apparatus of FIG. 1.

Referring now to the drawing in detail, and initially to FIG. 1, the basic devices employed for performing the method of the invention are a digester unit 30, a distillation and electrolysis unit 40, an electrical unit 50 including a power supply and controls, and a recorder 51 coupled to the controls in the electrical unit.

The digester illustrated in FIG. 2 includes a specimen holder 1 which is a modified test tube of polytetrafluoroethylene. Its open end may be closed by a cover 2 of the same material, and the specimen holder may be enclosed in a stainless steel pressure vessel 3 equipped with a threaded cap 3a. In the closed vessel 3, the cover 2 is hermetically sealed to the specimen holder 1 by a pressure plate 4 mounted in the cap 3a by a helical compression spring 4a. A capillary bore 3b in the cap communicates with the interior of the closed pressure vessel. The spring-loaded cover 2 thus acts as a safety valve for the specimen holder 1.

A well in an aluminum block 5 receives the loaded pressure vessel 3 during digestion. The temperature of the block 5 is sensed by a thermoelectric sensor 6 connected to the electrical unit 50 in a conventional manner, not shown, and the unit 50 energizes electricl cartridge heaters 7 in the block to maintain a digesting temperature that may be set on the unit 50. Cooling water nipples 8 on the block 5 may be supplied with cooling water for internally cooling the block. The flow of cooling water is controlled by the unit 50 by means of solenoid valves, not shown, as will presently be described.

The distillation and electrolysis unit 40 is illustrated in more detail in FIG. 3. As far as not explicitly described otherwise hereinbelow, it consists of thermally and chemically resistant glass. A distilling vessel 10 is attached by a ground glass joint to the lower end of a depending connecting tube 16 whose top communicates with the inner tube 17a of an upright reflux condenser 17 near the upper end of the inner tube. A drying tube 25 is connected to the enlarged top of the inner condenser tube 17a by another ground joint. It contains pumice 25a saturated with concentrated sulfuric acid. A glass tube 24 sealed into the lower end of the drying tube 25 terminates in a spherical nozzle 26 whose orifices are directed obliquely upward as not explicitly shown in the drawing. In the assembled condition of the apparatus, the nozzle 26 is received in the inner tube 17a and the free end of the glass tube 24 carries a tubulure accessible from the outside.

The open, lower end of the inner tube 17a is located near the bottom of a coaxial, tubular receiver 11 normally sealed by a polytetrafluoroethylene plug 18. Another connecting tube 13 branches from the top of the receiver 11 near the jacket of the condenser 17 in an obliquely upward direction and penetrates the interior of the wider tube 16. It then leads straight down through the lower end of the connecting tube 16 into the distilling vessel 10 and ends near the bottom of the vessel. The vessel 10 is received in an electrically heated block 15 analogous to the afore-described block 5, but not bored for receiving cooling water. The receiver 11 is arranged in a heating and cooling block 12 not significantly different from the block 5.

The condenser 17, receiver 11, and connecting tubes 13, 16 are of unitary construction, and a supply tube 9 sealed into the connecting tube 16 has an orifice vertically above the distilling vessel 10.

Figure 4:
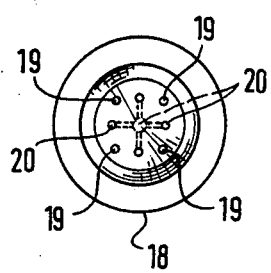
FIG. 4 illustrates a portion of the unit of FIG. 3 in enlarged top plan view.

The plug 18, shown in greater detail in FIG. 4, is pierced by four wires 19, 19' of 90:10 platinum-irridium alloy which normally project into the interior of the receiver 11 as electrodes. A manifold bore in the plug has four orifices 20 in the receiver and is connected to three tubes 21, 22, 23 extending outside the receiver 11.

Briefly, the afore-described apparatus is operated as follows:

A substance to be analyzed is digested in the sealed specimen holder 1 in a minimum volume of liquid acid medium at elevated temperature and pressure until the nitrogen in the substance is converted to ammonium ions. The digestion mixture is then transferred to the distilling vessel 10. Enough aqueous sodium hydroxide or other alkali is introduced through the tube 9 to make the mixture in the distilling vessel 10 alkaline, and an acidic aqueous medium, such as very dilute sulfuric acid, is introduced into the receiver 11 through the tube 24. The blocks 12, 15 are electrically heated while cooling water passes through the condenser 17. The temperature of the liquid in the receiver 11 is set at 190° to 210° C so that steam is discharged through the connecting tube 13 into the alkalinized digestion mixture in the distilling vessel 10 whose temperature is held at 100° to 140° C by the block 15. The ensuing steam distillation drives water vapor and ammonia from the vessel 10 through the connecting tube 16 into the inner tube 17a of the condenser 17 for ultimate absorption of the liquified vapors in the acidic liquid in the receiver 11. The temperatures of the blocks 12, 15 are controlled in such a manner that the volume of acidic aqueous liquid in the receiver 11 remains constant by balancing of the distillate received from the alkalinized digestion mixture in the vessel 10 by the amount of steam generated from the acidic aqueous solution and transferred to the vessel 10.

When the steam distillation is completed, the contents of the receiver 11 are cooled to a fixed temperature near ambient temperature, a buffer solution containing bromide ions is introduced through the tube 21, and the contents of the receiver 11, now weakly alkaline, are agitated by means of a gas stream introduced through the tube 22. The two electrodes 19 are connected to the power supply in the unit 50, and a constant current is passed through the weakly alkaline liquid to convert bromide ions to hypobromite ions which in turn oxidize the ammonia present to nitrogen. When the ammonia is completely destroyed, there is a sudden change in the current flowing between the two other electrodes 19' which are held at a constant potential difference. From the known strength of the constant current and the time for completion of ammonia oxidation, the nitrogen content of the specimen analyzed is readily determined, the constant current consumed being a measure of the original nitrogen content.

Referring now in detail to the individual steps of the procedure outlined above, it is evident that only reagents of at least analytical grade may be employed if extremely small amounts of nitrogen are to be determined, and that contamination with ammonia from the air of the laboratory is to be avoided.

Digestion of the specimen in a sealed container minimizes the amount of acid necessary and avoids contamination with atmospheric ammonia. If the amount of nitrogen to be determined is smaller than 10 $\mu g$, the digesting acid must be purified with particular care. Hydrofluoric, hydrochloric, and perchloric acid may be purified adequately at relatively low cost by isothermal distillation. Quartz distilling equipment is suitable for hydrochloric and perchloric acid, and hydrofluoric acid can be distilled in polytetrafluoroethylene equipment. Sulfuric acid is well suited for digestion, but is difficult to purify. Concentrated hydrogen peroxide solution may be added to the digesting acid to hasten the procedure. When the amount of nitrogen present is greater than approximately 10 $\mu g$, less painstaking purification of the acid may be permissible without introducing serious error.

Metals and organic substances can be digested adequately with 0.5 to 4 ml acid if the amount of the sample does not exceed 500 mg, as is usually the case. Such small amounts of acid are adequate because no acid can be evaporated during digestion. The temperature at which the digestion is performed will be selected to suit a material to be decomposed and the time available. Basically, temperatures between room temperature (about 18° C) and 180° C are suitable for most substances, but a lower limit of 50° C is preferred in most instances. Convenient decompositio temperatures for ferrous metals are between 120° and 140° C. Molybdenum and certain other metals are preferably digested at a starting temperature of 50° to 60° C which is gradually increased. It is generally preferred to digest the substance analyzed to the lowest temperature at which complete digestion can be achieved within a reasonable time. The low temperature extends the useful life of the specimen holder. Digestion periods may vary between 30 minutes and 12 hours. For a more detailed discussion of digesting conditions, reference may be had to Z. Anal. Chem. 260 (1972) 207–209.

The transfer of the digestion mixture from the specimen holder 1 to the distilling vessel 10 must be performed in an atmosphere practically free from ammonia, and the distilling vessel is quickly attached to the other elements of the distillation and electrolysis unit 40. A concentrated alkali metal hydroxide solution (20% to 40% by weight) is preferably employed for alkalinizing the digestion mixture. A 30% ± 3% sodium hydroxide solution is universally applicable and readily prepared by dissolving 300 g NaOH in one liter double-distilled water. The amount necessary may vary between 5 and 20 ml under extreme conditions, but it is normally feasible and preferred to employ a fixed amount of alkalinizing solution in consecutive analyses, and to select this amount between 10 and 15 ml ± 2%.

The aqueous acidic medium charged to the receiver 11 through the tube 24 is preferably dilute sulfuric acid, concentrations between 0.5% and 2.0% (by weight) being suitable under almost all conditions. It is normally practical to select a fixed concentration between 0.8% and 1.2% in a fixed amount between 1.5 and 2.5 ml, for example, 2.0 ml. Such a solution is readily prepared by diluting 1 ml 97% sulfuric acid to one liter with double-distilled water.

During steam distillation, the liquid level in the receiver 11 and/or the distilling vessel 10 is readily observed, and the heat supply to the blocks 12 may be controlled manually to maintain the original levels. If the level in the receiver 11 drops, the temperature in the block 15 enveloping the distilling vessel 10 is increased to hasten distillation into the receiver, and vice versa.

Temperatures closely approximating 125° C are generally suitable for the block 15 heating the distilling vessel 10, while a temperature of approximately 200° C in the block 12 is suitable under most conditions. Depending on the selected temperatures and other variables, the distillation of the ammonia is usually completed in 10 to 25 minutes, only rare conditions calling for a distillation period of more than 20 minutes.

The pH in the receiver 11 must be held at 8.6 ± 0.2 during the electrolytic conversion of bromide ions to hypobromite ions. Several suitable buffer solutions are known, sometimes available commercially, and may be modified to contain bromide ions. A very adequate buffer solution is prepared from 550 g potassium bromide, 20 g anhydrous sodium tetraborate, enough double-distilled water to make 1 liter, and an amount of sulfuric acid sufficient to produce the desired pH of 8.6 ± 0.2 when the buffer solution is mixed with an equal volume of the dilute sulfuric acid selected as an absorbent in the steam distillation step.

The current employed for converting the bromide to hypobromite ions may be selected freely. It is convenient to employ a power supply which will alternatively produce constant currents of 0.2067, 2.067, and 20.67 mA for three levels of sensitivity. The periods (in seconds) during which currents of the indicated strengths are permitted to flow between two electrodes 19 to oxidize all ammonia present to nitrogen are then a direct measure of the amounts of nitrogen originally present in the analyzed substance without requiring complex calculations.

The two electrodes 19' not employed for the electrolysis are connected to the power supply 50 to receive a very low potential, such as 100 mV, which does not affect the electrolytic oxidation of bromide ions, and are arranged in series circuit with a galvanometer. The current flowing between the indicating electrodes 19' rises abruptly when all ammonia is oxidized and the primary current passing through the solution produces bromine (see also Anal. Chem. 28 [1956] 440).

As will be evident from the preceding description of the method, the distillation and electrolysis stage may be automatized in an obvious manner, not illustrated, by providing solenoid valves in the supply lines for the tubes 9, 21, 22, 23, and 24, and by operating the valves in timed sequence. The temperatures in the blocks 12, 15 are sensed and maintained automatically in a known manner, but varied in response to changes in the liquid level in the receiver 11. The depth of liquid in the receiver affects the capacitance of a condenser constituted by the two indicating electrodes 19', and a signal derived from changes in the capacitance may be employed for secondary control of the temperatures in the blocks 12, 15.

In a typical automatic sequence, sodium hydroxide solution is supplied to the tube 9 from a storage container through a solenoid valve having a PTFE valve body and held in the open condition for a fixed period to supply a standard amount of alkalinizing liquid. Dilute sulfuric acid solution is similarly supplied through the tube 24 and nozzle 26. The liquid discharged obliquely upward from the nozzle 26 rinses the walls of the tube 17a and prevents gradual bild-up of distillation residues. The entry of ammonia into the tube 17a is prevented by the sulfuric acid in the pumice charge 25a. The blocks 12, 15 are supplied with controlled heating current to provide a desired distillation period of 20 minutes whereupon they are switched off.

Thereafter, cooling water is fed to the block 12, initially in very short bursts to avoid evolution of steam at a destructive rate by contact of the water with the block at its operating temperature of 200° C. The periods of water supply are gradually lengthened until steady flow of cooling water becomes feasible after about two minutes. The buffer solution next is introduced through the tube 21 by opening a solenoid valve for a fixed time, carefully purified nitrogen is introduced through the tube 22 as a stirring medium at a suitable rate (for example 300 ml/min.), and a potential of 0.1 V is impressed on two electrodes 19'. The current flowing between these electrodes is continuously recorded on a moving chart by one of the pens in the recorder 51. After a period sufficient to ensure thorough mixing of the contents of the receiver 11, such as 15 seconds, the other two electrodes 19 are connected to the power supply, and three additional pens of the recorder 51 start writing time indicia on the moving chart, the signals being derived in a conventional manner from the main supply of alternating current. 1-Second, 10-second, and 100-second periods are recorded. At the three current strengths indicated above, one second of electrolysis indicates the presence of 0.01, 0.1, and 1 $\mu$g nitrogen, and the nitrogen content of the analyzed substance is thus read directly from the chart.

If the gas stream agitating the electrolysis is constant, the automatic device described above produces closely reproducible results as will presently become apparent. It is necessary for highest precision to hold fluctuations in the gas pressure to within ± 2 millibar if the gas pressure is near 300 millibar.

At the completion of an analysis, the non-illustrated solenoid valve in the tube 23 is opened, and the contents of the receiver 11 are drained to waste. The receiver may then be rinsed with dilute acid from the nozzle 26 before the tube 23 is closed, and the apparatus is ready to receive another distilling tube 10 and the digestion mixture contained therein.

An operator's contribution to the operation of the apparatus described is limited to the supply and removal of distilling tubes 10, the selection of the electrolyzing current for the expected range of nitrogen content in the digested sample, and the pushing of a starting button.

The following Examples are further illustrative of the method of the invention and of the capability of the apparatus described.

EXAMPLE 1

Instead of a digestion mixture, the distilling vessel 10 in the apparatus shown in FIG. 2 was charged with carefully prepared and precisely dosed solutions of ammonium chloride, and ammonia was distilled from the alkalinized solutions for 20 minutes as more fully described above. Fifteen tests were performed with each of four solutions containing 0.10, 0.50, 1.00 and 10.00 $\mu$g nitrogen respectively. The mean values and standard deviations of the 15 tests for each level of nitrogen were 0.098 (0.013), 0.50 (0.03), 0.99 (0.04), and 10.0 (0.10) respectively.

EXAMPLE 2

Twelve specimens of a standard grade of steel containing nominally 120 ± 5 p.p.m. nitrogen and weighing between 80 and 150 mg were digested each overnight in 2 ml of a 10:1 mixture (by volume) of concentrated hydrochloric acid and perchloric acid at 120° C in the apparatus of FIG. 2, and the digestion mixtures were worked up in the apparatus of FIG. 3.

The mean value of the 12 analyses was 120 p.p.m. nitrogen, the standard deviation 4 p.p.m.

EXAMPLE 3

Nine specimens of a standard grade of steel containing nominally 29 ± 5 p.p.m. nitrogen and weighing 80 to 130 mg were digested and further worked up as in Example 2. The mean value of the nine analyses was 28 p.p.m, the standard deviation 2 p.p.m.

When 11 smaller samples of the same material were analyzed (8 to 17 mg), the mean value of the analysis results was 29 p.p.m., the standard deviation 4 p.p.m.

EXAMPLE 4

A mixture of 10 parts by volume concentrated hydrofluoric acid and one part concentrated perchloric acid was used at 140° C for digesting eight specimens of tantalum powder, 11 specimens of niobium wire, and 20 specimens of niobium powder, and the several digestion mixtures were worked up by steam distillation and electrolysis as described above.

The tantalum powder was reported by the supplier to contain 29 p.p.m. nitrogen as determined by Kjeldahl digestion and photometric determination of ammonia in the distillate of the alkalinized digestion mixture. The 8 specimens weighed 150 to 210 mg and were found by the method of this invention to contain an average of 31 p.p.m. nitrogen, the standard deviation being 6 p.p.m.

The niobium wire was reported by the supplier to contain 250 p.p.m. nitrogen. The 11 specimens tested varied in weight between 25 and 50 mg and averaged 258 p.p.m. nitrogen at a standard deviation of 20 p.p.m.

The niobium powder reportedly contained 30 p.p.m. nitrogen, and the 20 specimens gave an average nitrogen content of 23 p.p.m. with a standard deviation of 4 p.p.m.

EXAMPLE 5

Nine specimens of zirconium weighing between 140 and 160 mg were digested in the same acid mixture as in Example 4. The temperature of the acid was gradually increased from room temperature to 140° C over a period of 30 minutes. Distillation and electrolysis were performed as described above, and the nine analyses averaged 32.9 p.p.m. nitrogen with a standard deviation of 1.2 p.p.m.

When the perchloric acid was replaced by 30% hydrogen peroxide solution in a second series of otherwise analogous tests on the same material, the results obtained were not significantly different.

EXAMPLE 6

Five copper specimens weighing 300 to 350 mg were each digested overnight in a mixture of 10 parts concentrated hydrochloric acid and one part concentrated perchloric acid at 140° C, and the digestion mixtures were worked up in the manner described. The test results averaged 0.7 p.p.m. nitrogen, and the standard deviation was 0.1 p.p.m.

The results indicated above are typical of those achieved by the method of the invention with a wide range of substances. The relatively wide spread of analysis results partly indicated by high values of standard deviation in Example 4 are believed due to inhomogeneity in the tested material because similarly unusual variations were observed in analyses of the same metals for oxygen and carbon.

The nitrogen content of organic compounds is normally higher by one or more decimal orders of magnitude than that of metals, and the method of this invention is applied to organic substances to highest advantage only where the amounts of material available for analysis are extremely small. The results of nitrogen determinations performed according to this method are reproducible within limits of ± 30 ng. 0.1 μg Nitrogen is determined with a variation coefficient of about ± 15%, and amounts of 10 to 1000 μg with a variation coefficient of less than ± 1%.

While the invention has been illustrated particularly in its application to metals in which minute amounts of nitrogen critically affect performance, it is applicable without significant change to the analysis of minerals, organic substances of all kinds, water, waste water, and many more in an obvious manner. It is particularly well suited for determining the composition of standard samples employed for calibrating spectrographic apparatus.

What is claimed is:

1. Apparatus for analyzing a substance for nitrogen content comprising:
    (a) a vessel adapted to hold a medium prepared by digesting said substance in a liquid medium until the nitrogen content thereof is converted to ammonium ions and alkalinizing said medium;
    (b) first heating means for heating the contents of said vessel to a temperature above the boiling point of water and for thereby generating vapors from said contents;
    (c) a receiver adapted to hold an acidic aqueous medium;
    (d) second heating means for heating the contents of said receiver to a temperature higher than the boiling point of said acidic aqueous medium and for thereby generating steam;
    (e) first connecting tubing connecting said vessel to said receiver for introducing the material of said vapors into the acidic medium in said receiver;
    (f) second connecting tubing connecting said receiver to said vessel for introducing steam generated in said receiver into said contents of said vessel;
    (g) condenser means interposed between said first connecting tubing and said receiver for condensing said material of said vapors; and
    (h) a plurality of electrodes projecting into said receiver, said vessel, said receiver, said first tubing, said second tubing and said condenser means constituting a closed system sealed from the ambient atmosphere.

2. Apparatus as set forth in claim 1, wherein said plurality of electrodes includes four electrodes insulated from each other.

* * * * *